(12) United States Patent
Ragless

(10) Patent No.: US 6,782,909 B1
(45) Date of Patent: Aug. 31, 2004

(54) MATRIC POTENTIAL RESPONDER IMPROVEMENTS

(76) Inventor: Clive Lindsay Ragless, Unit 26, 5-11 Colley Terrace, Glenelg, South Australia, 5045 (AU)

( * ) Notice: Subject to any disclaimer, the term of this patent is extended or adjusted under 35 U.S.C. 154(b) by 0 days.

(21) Appl. No.: 09/857,990
(22) PCT Filed: Dec. 21, 1999
(86) PCT No.: PCT/AU99/01132
§ 371 (c)(1),
(2), (4) Date: Jun. 11, 2001
(87) PCT Pub. No.: WO00/37935
PCT Pub. Date: Jun. 29, 2000

(30) Foreign Application Priority Data

Dec. 21, 1998 (AU) ............................................... PP7817

(51) Int. Cl.⁷ ............................................... A01G 25/02
(52) U.S. Cl. ........................................ 137/78.3; 239/63
(58) Field of Search ............................ 137/78.3; 239/63

(56) References Cited

U.S. PATENT DOCUMENTS

| | | | |
|---|---|---|---|
| 3,867,837 A | * 2/1975 | Malin | ............................ 73/73 |
| 3,874,590 A | 4/1975 | Gibson | .......................... 239/63 |
| 4,182,357 A | 1/1980 | Ornstein | ........................ 239/63 |
| 4,648,555 A | 3/1987 | Gumbmann, Jr. | ............. 239/63 |
| 4,655,076 A | 4/1987 | Weihe et al. | ................... 73/73 |
| 4,696,319 A | 9/1987 | Gant | ........................... 137/78.3 |
| 4,989,628 A | 2/1991 | Gil et al. | .................... 137/78.3 |
| 5,148,825 A | 9/1992 | Gil et al. | .................... 137/78.3 |
| 5,273,066 A | * 12/1993 | Graham et al. | ............. 137/78.3 |
| 5,329,081 A | 7/1994 | Jones | ....................... 200/61.04 |
| 6,220,268 B1 | * 4/2001 | Bolton et al. | .................. 137/14 |

FOREIGN PATENT DOCUMENTS

WO    PCT/US97/15049    2/1998

* cited by examiner

Primary Examiner—A. Michael Chambers
(74) Attorney, Agent, or Firm—R. Neil Sudol; Henry D. Coleman; William J. Sapone

(57) ABSTRACT

A matric potential responder which includes a liquid absorbing swellable nonliquid material (115) held within a housing (114) of a ceramic material environ such as soil, to the material (115), being subject to a compressive force such as a spring (116). This uses balance of compressive force as compared to tension of the soil matric potential being used to control a position of a valve (119) which is arranged to effect an output such as control of a mains water valve (110).

24 Claims, 14 Drawing Sheets

Figure 1:
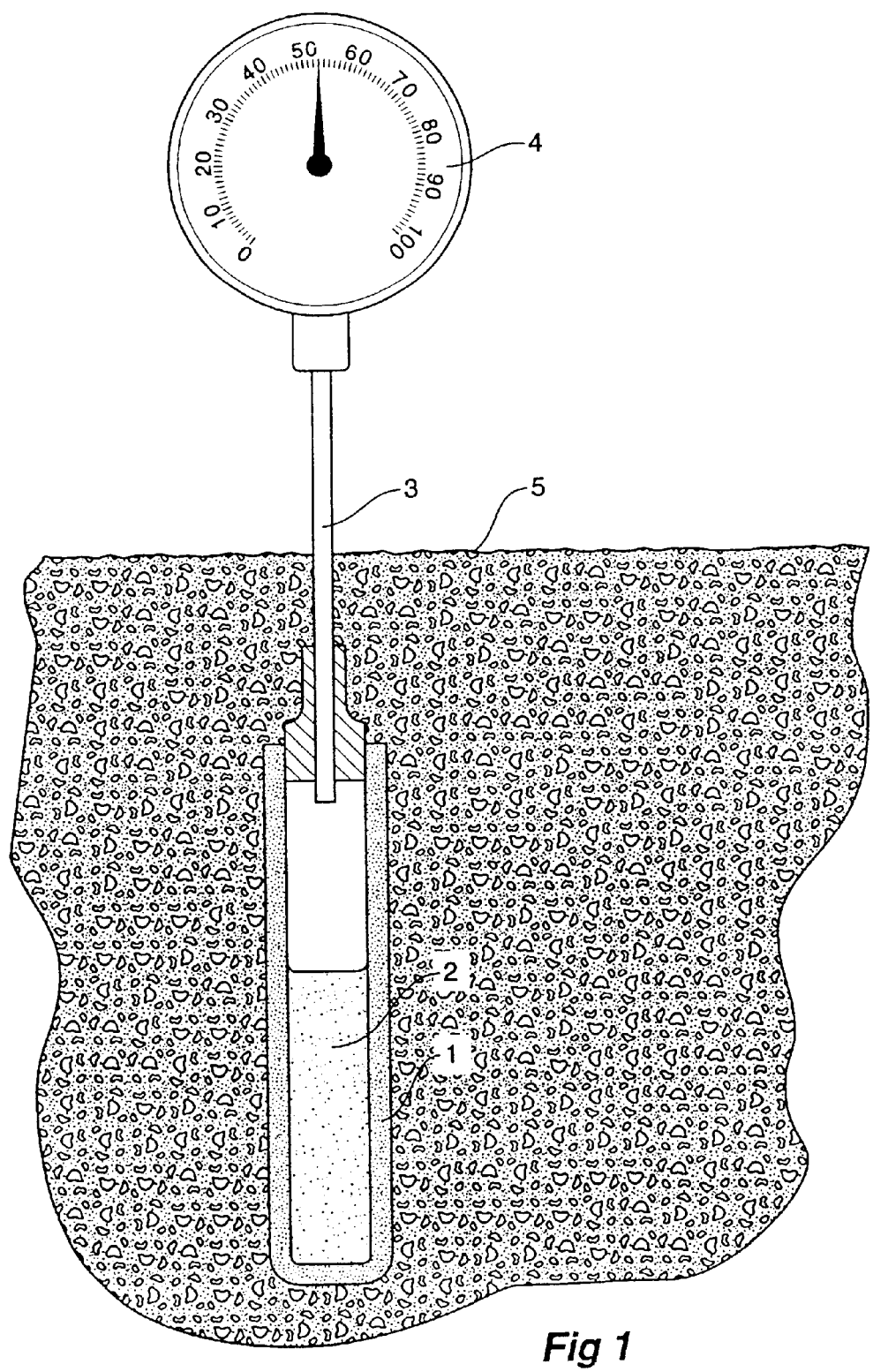

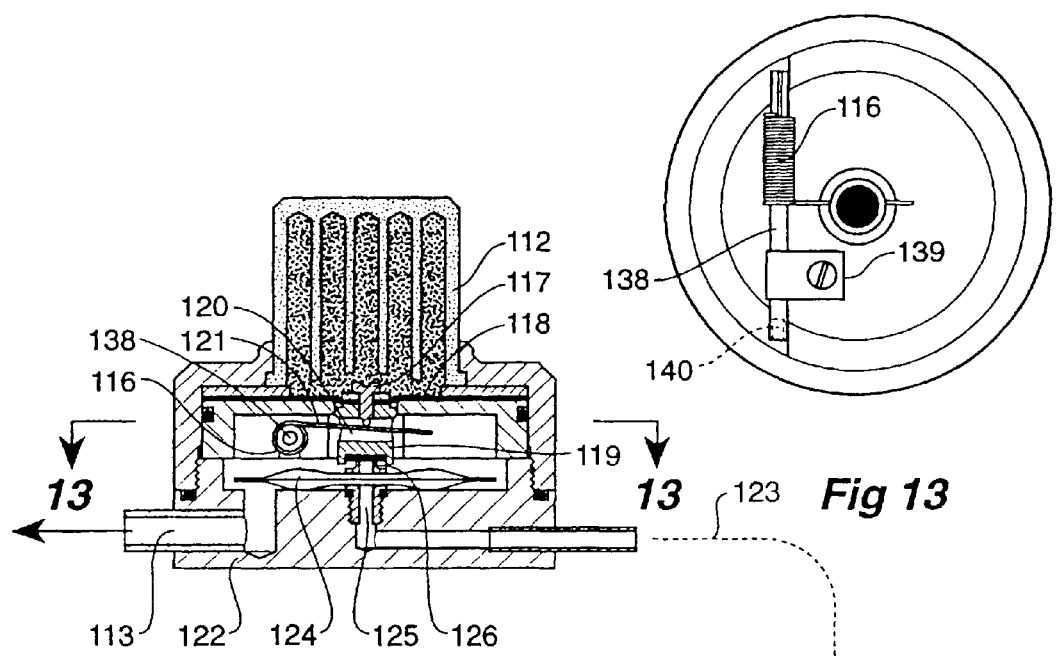
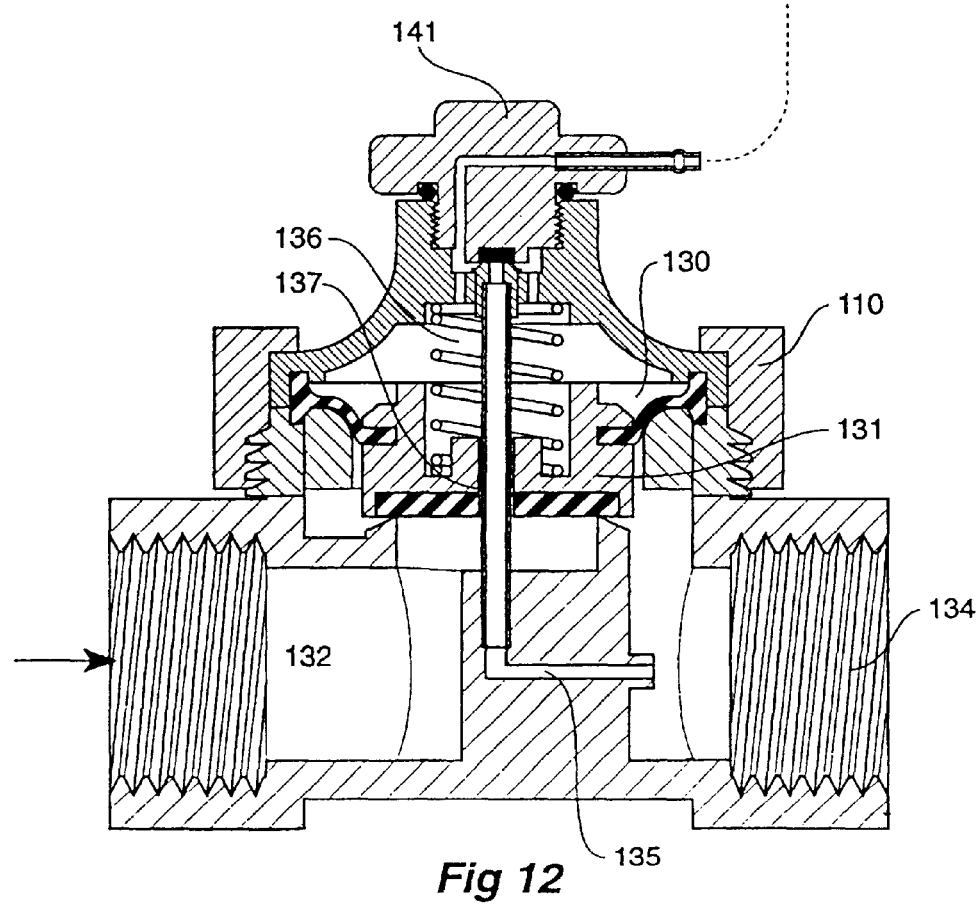
Fig 13
Fig 12

MATRIC POTENTIAL RESPONDER IMPROVEMENTS

FIELD OF THE INVENTION

This invention relates to an apparatus and a method for effecting a response to the matric potential of a medium such as soil which can be useful as a measurement or as a control for water supply.

This then may include a matric potential responder, an actuator for use in a responder, a sensor for use in a responder and method of measuring matric potential.

BACKGROUND OF THE INVENTION

It is known to measure some factors of soil to establish some guide to an amount of water that might exist in soil to facilitate growth of plants in that soil.

There are accordingly devices measuring the electrical resistance of the soil, the electrical impedance of the soil or even the dielectric constant of the soil, each of which measures are useful in some cases but do not however provide a measure of matric potential.

Plants derive access to moisture in soil by overcoming matric potential in the soil or as it is sometimes termed "soil suction".

Such a characteristic is currently able to be measured by a tensiometer but there are significant difficulties with any known tensiometer. One such difficulty but not the only difficulty is that a tensiometer is not useful outside of a relatively small range of matric potentials (zero kilopascals through to 80 kilopascals) which range is substantially less than would be useful to assist in assessing water availability for plants.

An object of this invention is to provide a further method and apparatus by which matric potential can be measured or used to assist in watering functions for plants which can at least provide an extended range of measurement or response and which, at relatively small cost, can provide with reasonable accuracy such response or measurement.

It is previously known to use a water swellable material which when put in contact with water will swell and then use this effect to close a valve supplying water.

Hitherto, most such proposals have described a water swellable material as a material that will, in the presence of sufficient water, swell so that given enough time and enough water the extent of swelling will be sufficient to close a valve against significant resistance or trigger a release against a substantial amount of resistance, with the trigger then further releasing some valve or other operation for control of water supply.

Such previous applications then seem to treat the use of such material as simply a detector of the presence of water so that with water present and given sufficient time and generally total water inundation this change in status of the material from not swollen to swollen or the opposite, can then be used to trigger some control either directly or indirectly.

In serious water use applications such an approach has serious deficiencies. It does not, for instance, provide for commencement of watering in conditions which are ideal for the plant where any drying beyond perhaps matric potential of 150 kilopascals is undesirable. If one cannot measure this then it is an open question as to when a start might occur and this is simply unacceptable for serious watering of plants.

Such devices that I have previously seen proposed, then, are not set up to or do not respond to take account of the matric potential of the medium to an extent that makes them useful for serious control of watering.

SUMMARY OF THE INVENTION

I have found that it is possible to measure matric potential using water swellable non-liquid materials and further more use these materials to then usefully control supply of water for serious watering purposes. This discovery results from an understanding of what seems to be a basic characteristic of such materials. If the material is exposed to a selected value of matric potential then this will effect an internal suction effect within the whole of the material. If we then apply a measured external force to the material which has the effect of applying throughout the material a compression, then soil suction effect or matric potential within the material will be offset by this compression.

In one form this invention can be said to reside in a matric potential responder which includes a liquid absorbing swellable material which will exhibit an internally developed increase or decrease in expansive pressure within the material in response to the matric potential of hydraulically connected soils or other medium, means applying and/or maintaining a compressive pressure to the said material, and means adapted to effect an output in response to changes in respect of the internal pressure of said material.

In preference, the material selected and the compressive pressure applied are such that the responder will provide an output to detected matric potential within the range of from 50 kilopascals to 300 kilopascals.

In preference the matric potential responder includes a housing at least one part of the housing being porous to provide for the effect of matric potential within liquid to be able to transfer therethrough, and within the housing, a liquid absorbing swellable material which will exhibit an internally developed increase or decrease in expansive pressure within the material in response to the matric potential of the hydraulically connected materials, means to apply compressive pressure to the said material within the housing, and means adapted to effect an output in response to changes in respect of the internal pressure of said material.

In one preferred form, there is a ratio of hydrogel to container or housing volume which will result in an internally generated pressure so that with unlimited access to water such that pressure will be 200 kilopascals. There is provided a piston with a limit to its outward movement subject to a resilient pressure such that an externally applied pressure will be 100 kilopascals to the material.

When the hydrogel is exposed to a matric potential of greater than 100 kilopascals, the piston will displace the material to an extent resulting in a change of volume and inward movement of the piston dependent upon the extent of the soil matric potential to which the hydrogel is exposed. This movement can be utilized by connecting it to other mechanisms for indicating and control purposes.

With a housing defining a substantially fixed volume, a change in matric potential of swellable material held confined by the housing will be exhibited by a change in internal pressure within the material. Such a change in pressure is generally linear with respect to the change in matric potential. (This can be compared to difficulties of using a volume change which will be generally non-linear with respect to matric potential).

In preference, the pressure applied is such that the externally applied pressure will be such that the physical pressure other than through the matric potential change will be approximately 300 kilopascals.

In a further form, in preference, there is a pressure transducer within the material such that any change in pressure within the material will be directly detected by the electrical transducer which in turn then can provide an electrical effect in accordance with the detected magnitude and/or change in pressure.

In another preferred arrangement, the material is subjected to a head of liquid by being separated from the material by a flexible membrane and such then that the head of liquid which can be open to atmosphere, will then exhibit a change in height in response to a change in pressure within the material which in turn depending upon the characteristic of the particular material, will expand or contract in accordance with the externally detected matric potential of the medium within which it is located.

In preference, such liquid to exhibit a change in pressure should be of high specific gravity so that liquid mercury can be used so that the upper most head of the mercury can then be calibrated in accordance with changes in expansion of the material which in turn are caused by a change in internal pressures in accordance with the balance of matric potential effected.

In such an example, the liquid itself provides the first pressure to establish a physical state of the material so that any externally detected matric potential will reduce the internal pressures within the material proportionately.

For instance, if the material is pressed to be 300 kilopascals, and it is put into hydraulic communication with soil having 100 kilopascals matric potential, then this will reduce the volume of the material to a 400 kilopascals volume.

Such a change can then be detected by detecting the volume change of the material for example by a simple sight glass.

In preference, the housing including or being totally comprised of a porous material has for its purpose to provide for a hydraulic communication which will allow the transfer of matric potential between the materials on respective sides of the porous material and to ensure a stable volume so that the volume change of the swellable material will be reliably transferred to the measuring means.

Baked and unglazed ceramic materials conventionally exhibit this characteristic and in experiments so far have shown to be appropriate.

Ceramic material is substantially rigid so that changes within the internal pressure of the material held with at least one part against the ceramic will not unduly deflect the ceramic so that the position of other portions of the material can be used to gauge the effect of the change in internal volume.

The ramifications of these steps and features are very high indeed.

Conventionally, a tensiometer is simply filled with water and when in a medium exhibiting more than 80 kilopascals suction, this will cause the water within the housing of the tensiometer to potentially break into a vacuum status dependent upon the vapor pressure of the water at the time and therefore be no longer useful to measure any different or extended suction range.

Growing plants mostly access water when held within a range of matric potential from 0 kilopascals to 300 kilopascals (they can less comfortably access water from soil at over 1,500 kpa) within the soil so that the one conventional technique of measuring soil suction is not useful outside of a small portion of the range of suction that should be able to be detected.

The discovery of this invention is that we need no longer be subject to the difficulties associated with the previously known simple tensiometer.

Accordingly this is because liquid preferably within an appropriate porous housing is held by a medium which, of itself, exhibits an internally compressive pressure and is exhibiting this effect by reason of molecular attraction within the structure of the material.

It will be readily appreciated that many different approaches can now be used to apply this concept to a number of various responders both for the purpose of effecting an output that of itself can be used to perform work by way of directly changing the open or closed status of a valve or in another form, have the pressure directly detected to effect either an electrical or visual output in response to such detected pressure changes in response to changes in the matric potential effect.

It is to be understood that what is being described is different from something which merely uses a material which will expand when wet and which will contract when dry.

The material that is to be used is something that can exhibit a structure which will provide a force with the effect that water will be held against an externally applied force and will give up that water with the extent of that force.

It has been found that a material which is a solid hydrogel can be used as one example, and in another example, a material which can absorb so much water as to be essentially fluid like, nonetheless can also exhibit the necessary characteristics.

If the material is to be solid, in preference, there are arrangements firstly to ensure that there is an effective hydraulic connection to the material from the porous barrier and further the solid material is arranged so that any pressure changes internally will result in a predictable expansion or contraction or change in pressure or in these all which can then be used to accurately assess the effective result.

In practice this has meant that the material can be in the form of thin disks which are flat and stacked one upon the other with sheets of interlocking fibrous material therebetween with solid plates such as metal, plastic or ceramic plates therebetween. Most of the transverse to the planar direction of the disk shape will expand or contract in response to the detected change in matric potential with the planar direction expansion being inhibited substantially to an extent that the volume is constrained howbeit with interleaving fibrous sheets.

The interleaving wicking material is arranged to extend to a side of the stack to be in contact with the material for matric potential transfer. In another approach, there is a solid material which is however divided with a number of slots which are filled with wicking material or at least material that will transfer liquid to provide a matric potential communication.

Figures 2, 3:
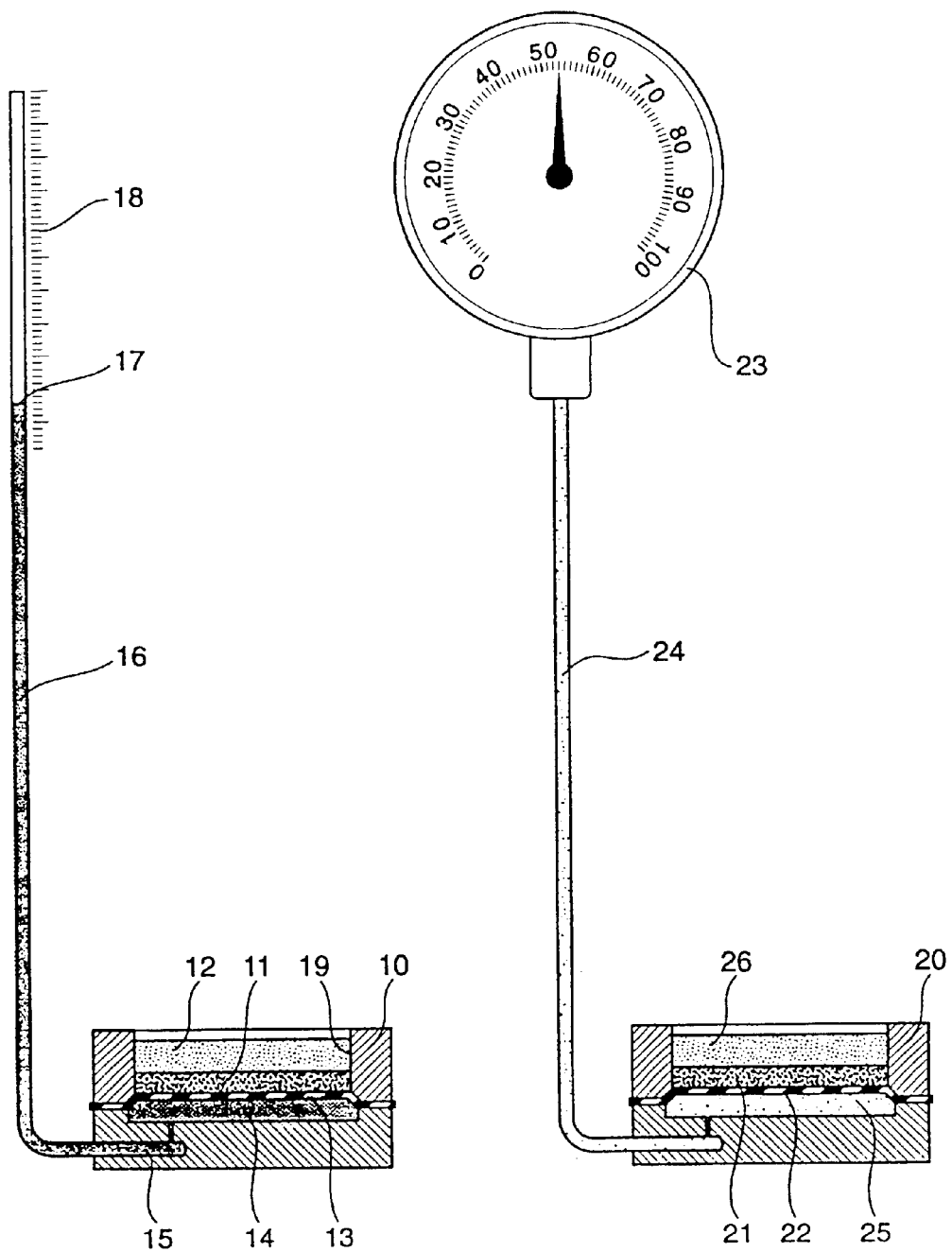
Figure 4:
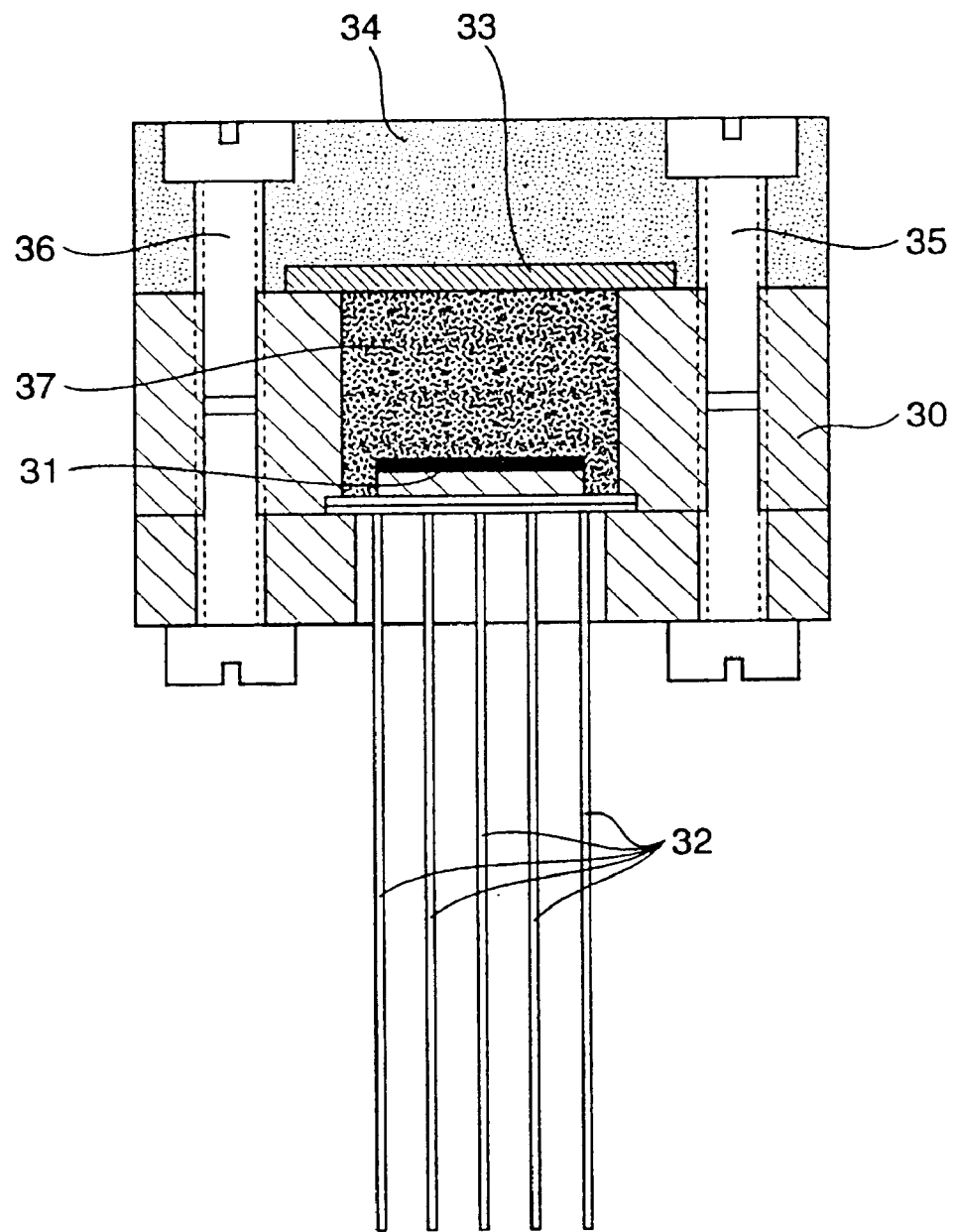
Figure 5:
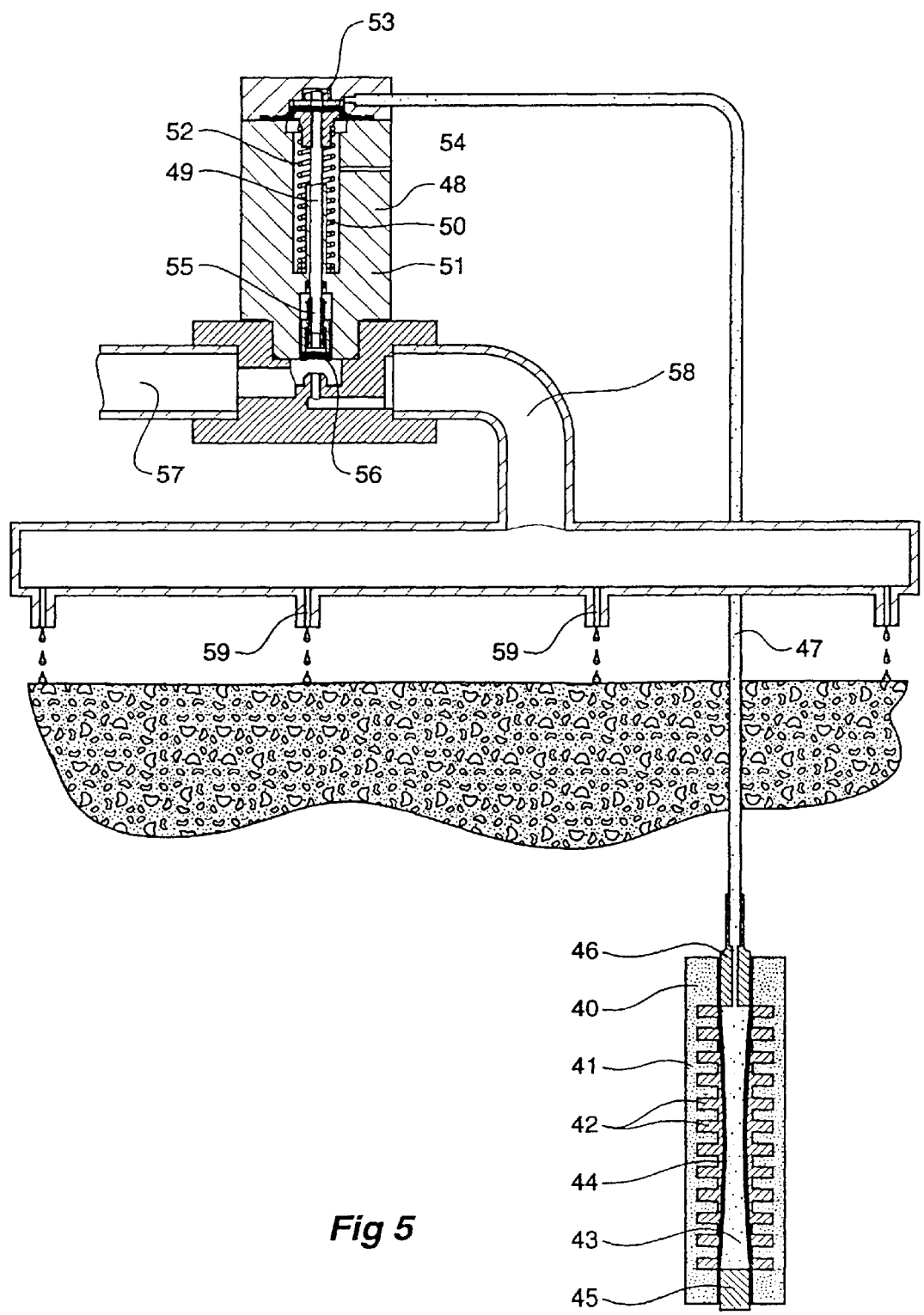
Figure 6:
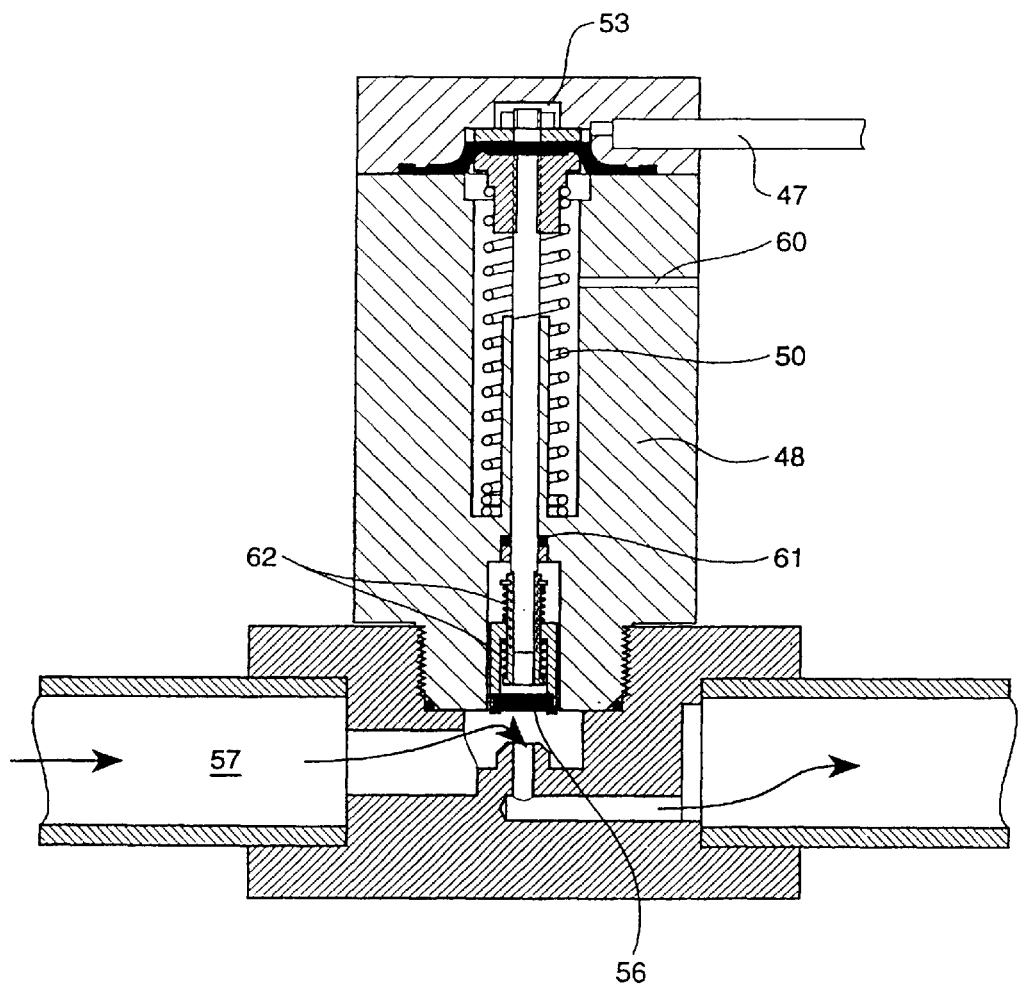
Figure 7:
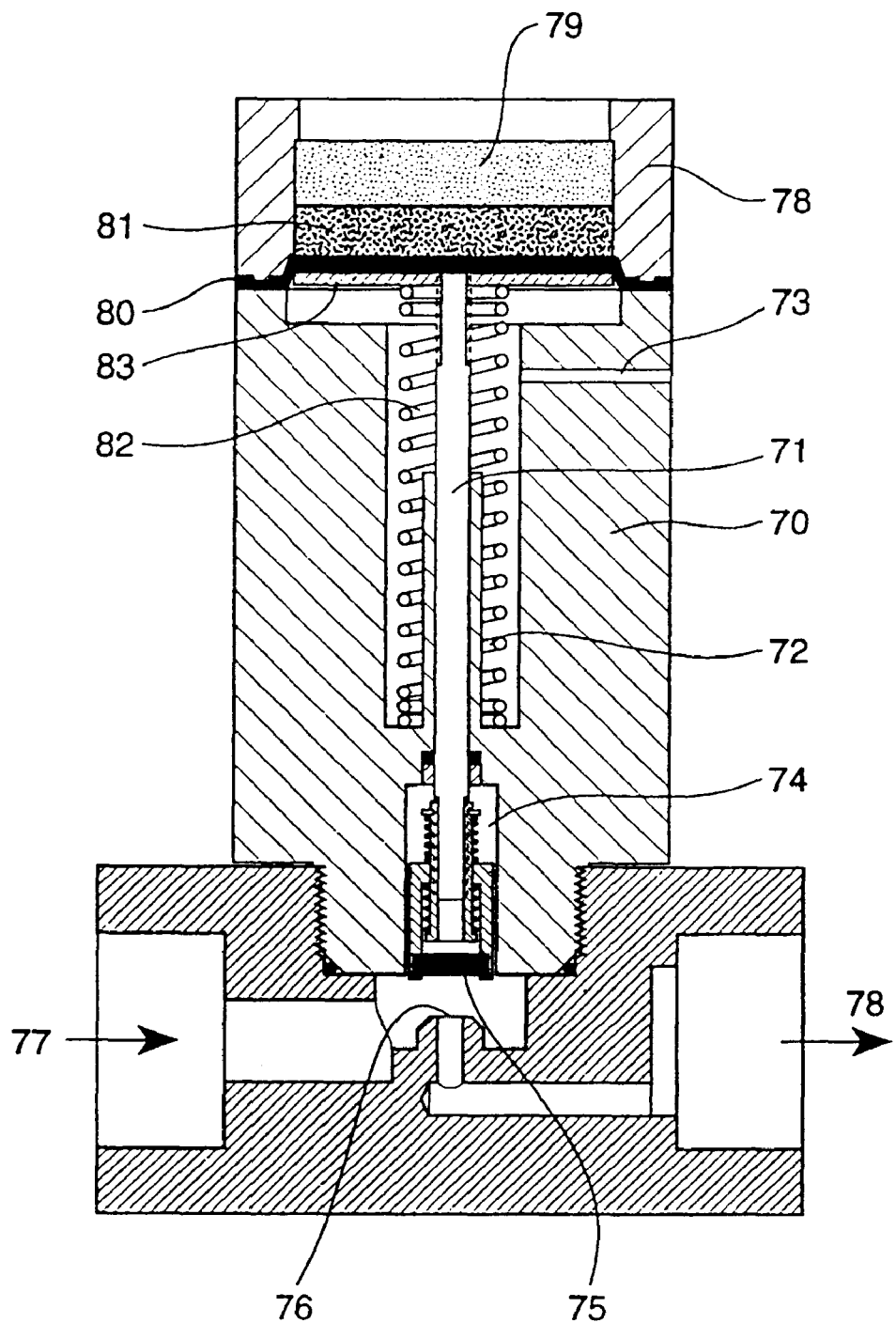
Figure 8:
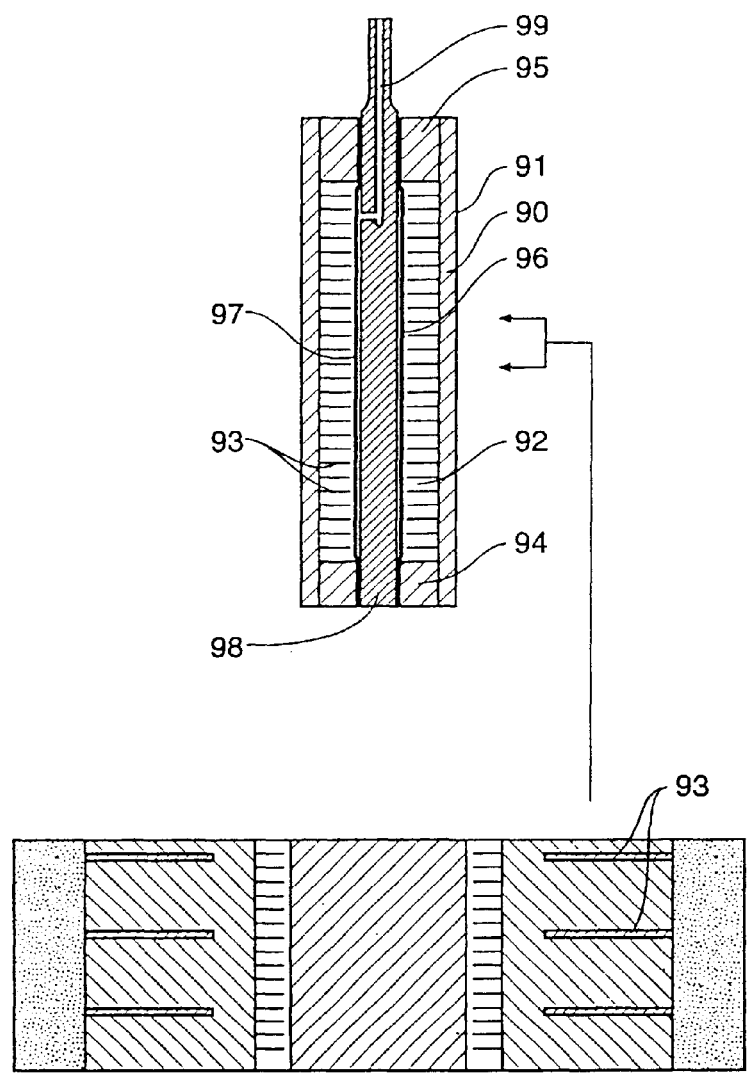
Figure 9:
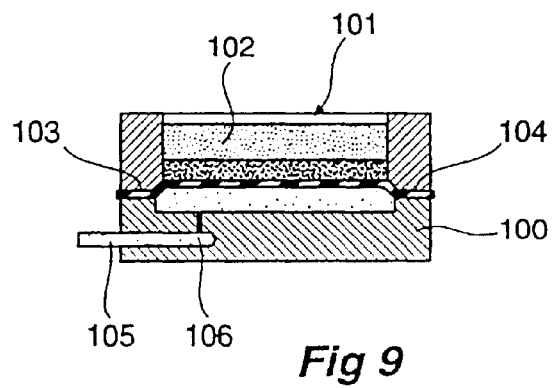
Figure 11:
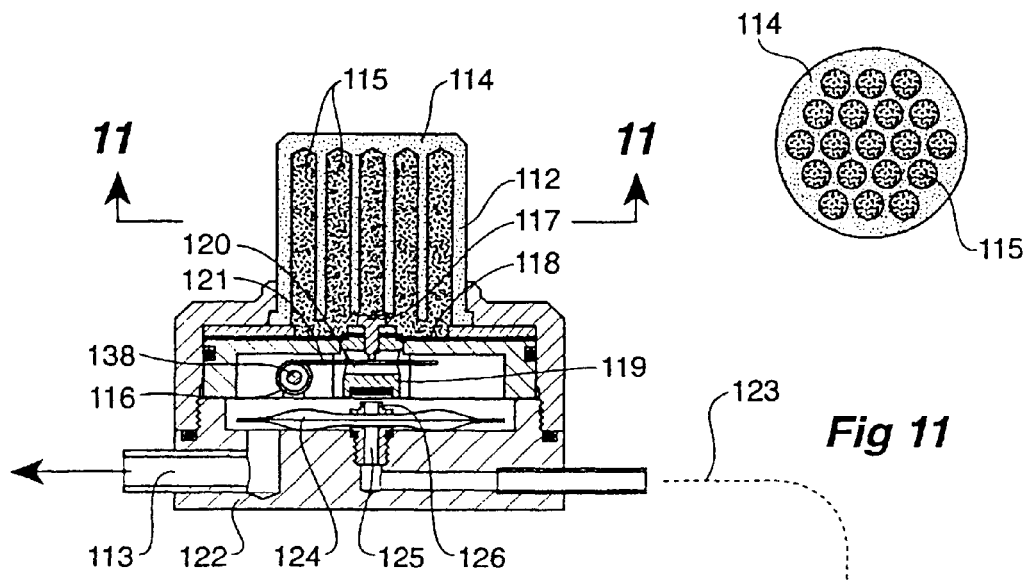
Figure 10:
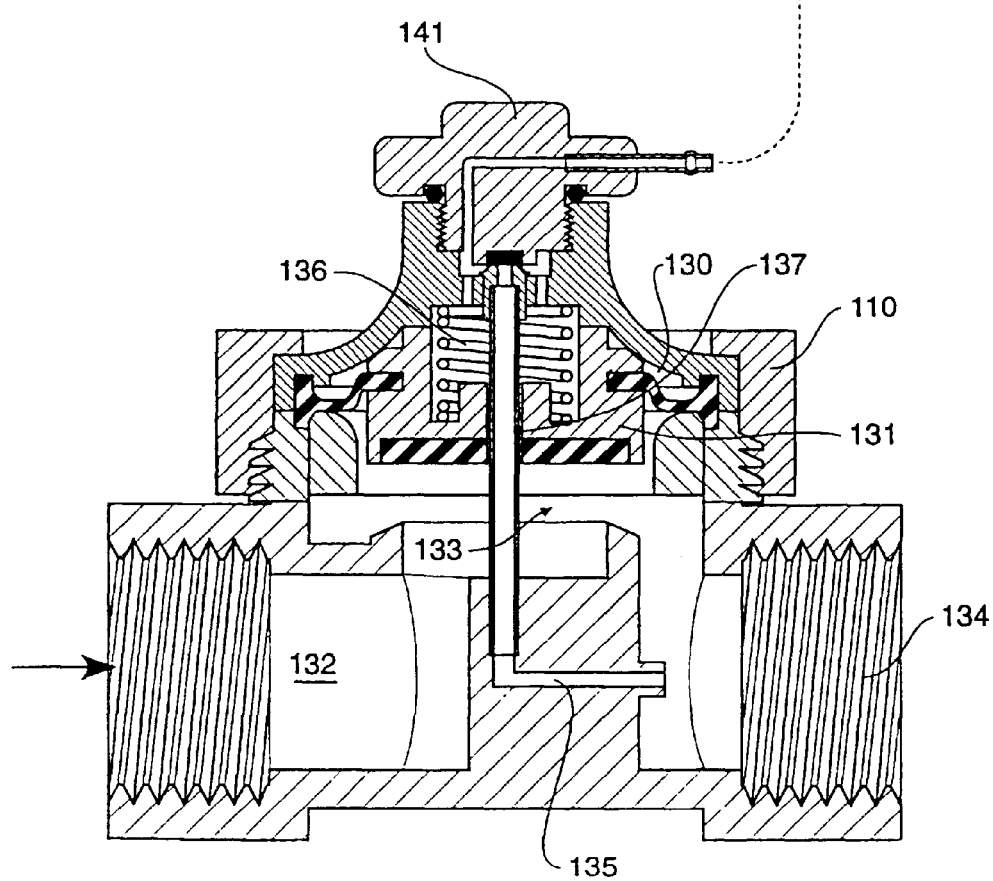
Figure 14:
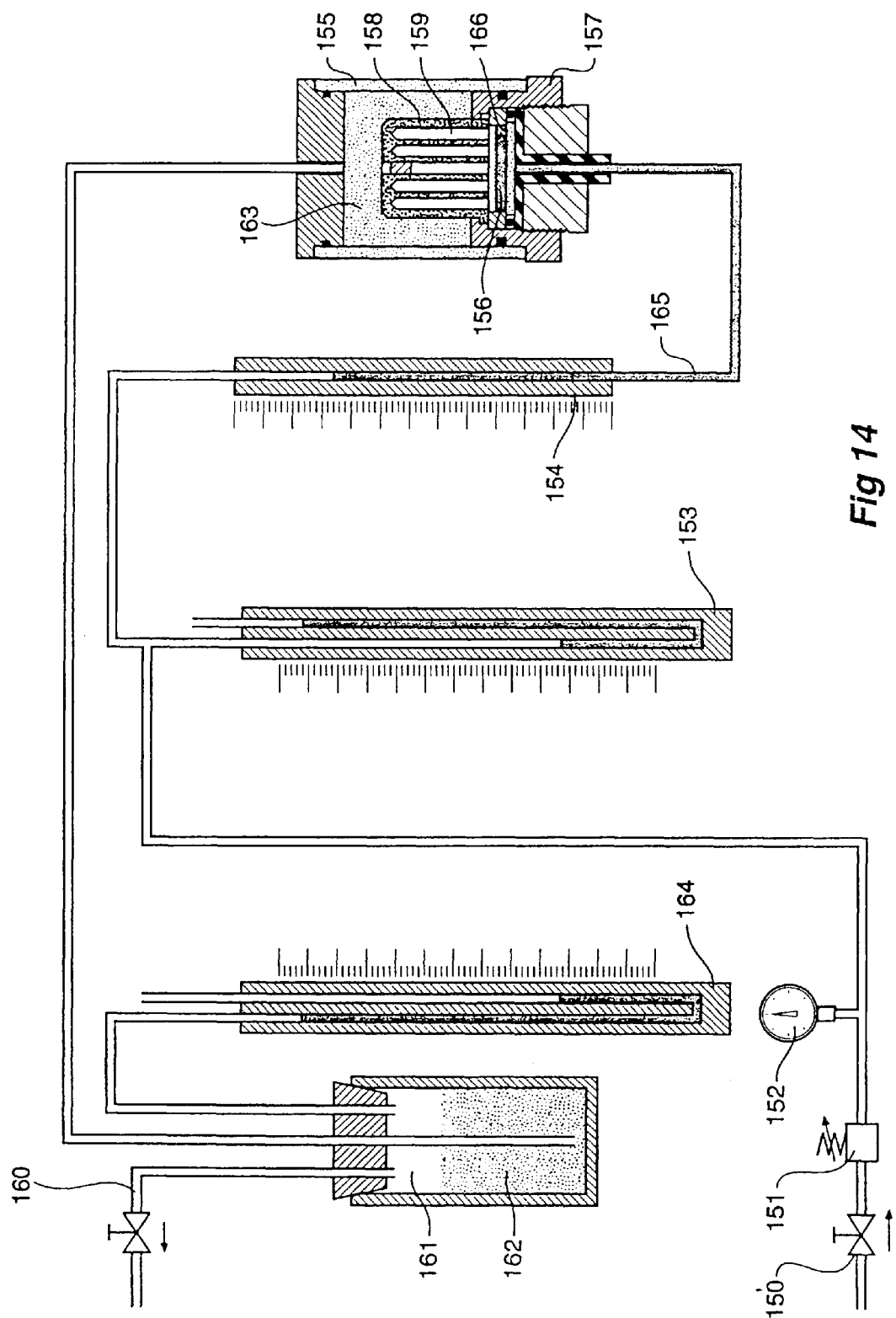
Figure 15:
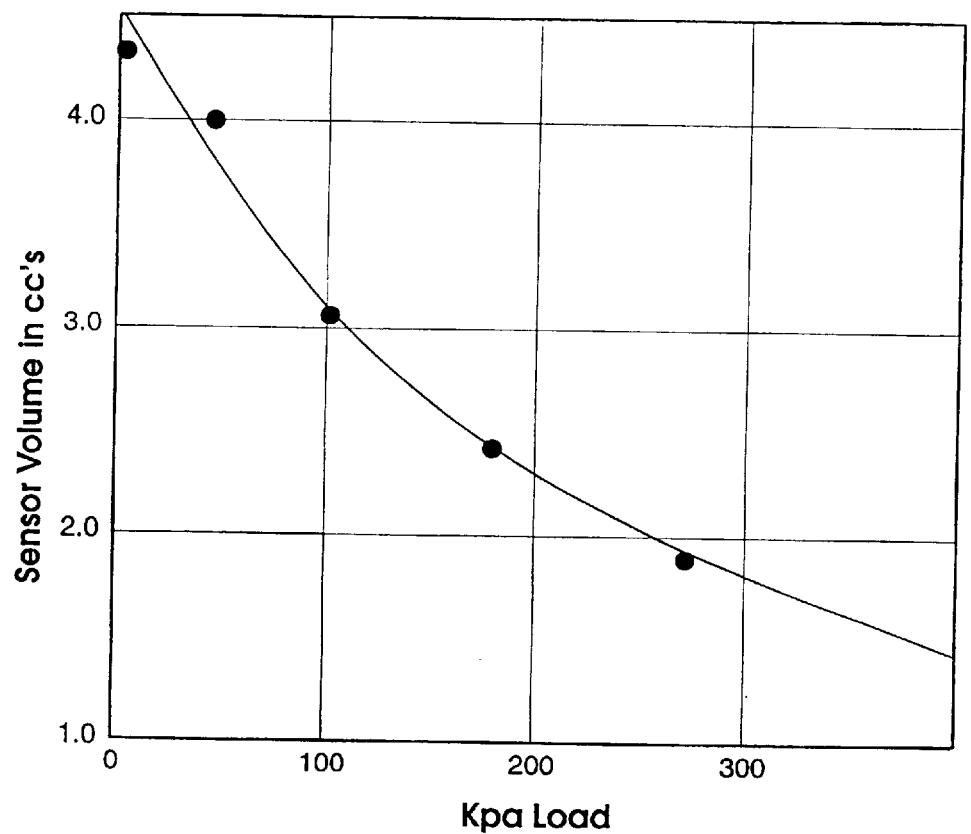
Figure 16:
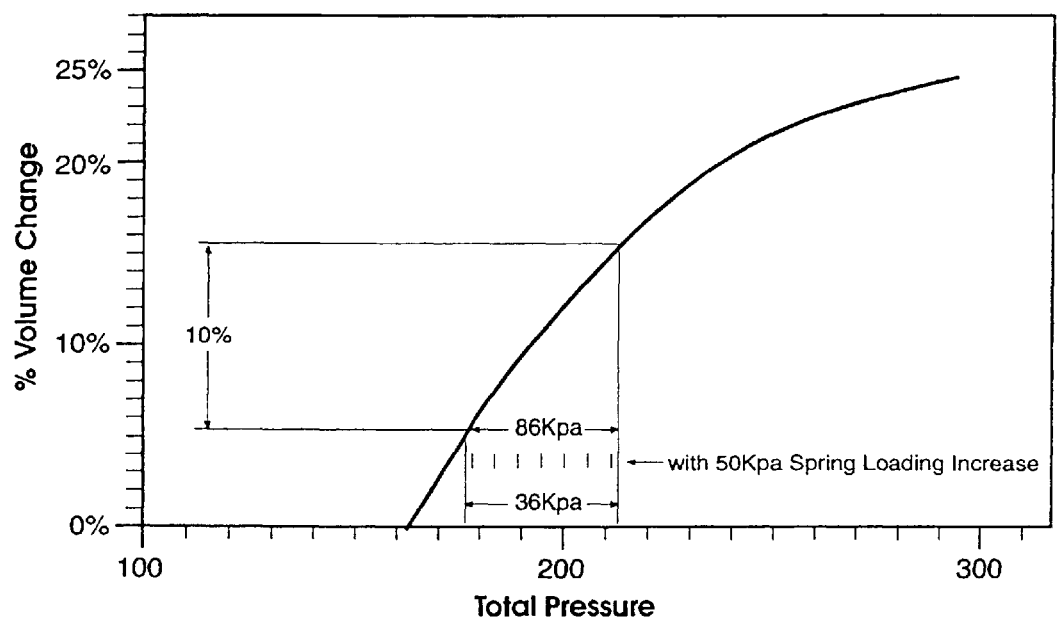

For a better understanding of this invention it will now be described with reference to preferred embodiments which shall be described with the assistance of drawings wherein FIG. 1 is a cross sectional view of a conventional tensiometer, FIG. 2 is a first embodiment showing a constrained water swellable material within a housing and a manometer pressure responding arrangement, FIG. 3 is a second embodiment which is substantially the same as in FIG. 2 except there is a Bourden tube pressure measuring device providing a responding arrangement, FIG. 4 is a third embodiment with hydrogel constrained along one side by a porous ceramic and against an opposite side a slug of pressure transmission material to an electrical pressure transducer, FIG. 5 is a schematic cross sectional view of a responder arrangement being a fourth embodiment including a soil matric responder connected to an actuator controlling a water distribution arrangement, FIG. 6 is an enlarged view of the actuator as shown in FIG. 5, FIG. 7 is a cross sectional view of a fifth embodiment of an integrated responder water flow controller, FIG. 8 is a cross sectional view of a sixth embodiment of an alternate sensor that can be used in the arrangement of the fourth embodiment, FIG. 9 is a cross sectional view through a further sensor that can be used in the arrangement of the fourth embodiment, FIG. 10 is a cross sectional view through a responder in accordance with a seventh embodiment showing this when responding to a dry state, FIG. 11 is a cross sectional view through the sensor along the lines of 11—11 of FIG. 10, FIG. 12 is a cross sectional view through the responder in accordance with the seventh embodiment as shown in FIGS. 10 and 11 but showing this when responding to a wet state, FIG. 13 is a cross sectional view through the sensor of FIG. 12 along the lines of 13—13, FIG. 14 is a schematic view in cross section of the apparatus used to test the responses of various matric potential responding materials, FIG. 15 is a graph of a relationship plotted between the hydrogel (polyacryalmide) volume and a load applied to that hydrogel in Kilopascals, FIG. 16 is a graph of a result matching % volume change with total pressure applied to the hydrogel material (polyacrylamide). Sensor volume changes will decrease with the spring loading of the piston so that if the additional load increases by 50 kpa then an additional 50 kpa of change in sensor pressure will be required to effect a 10% change in volume.

Figure 17:
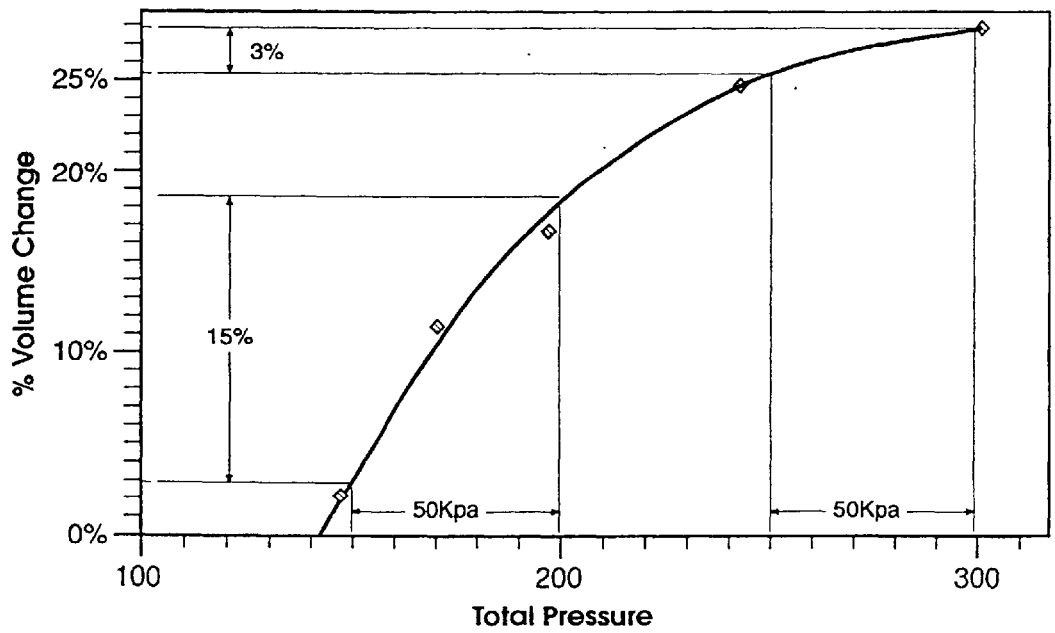
Figure 18:
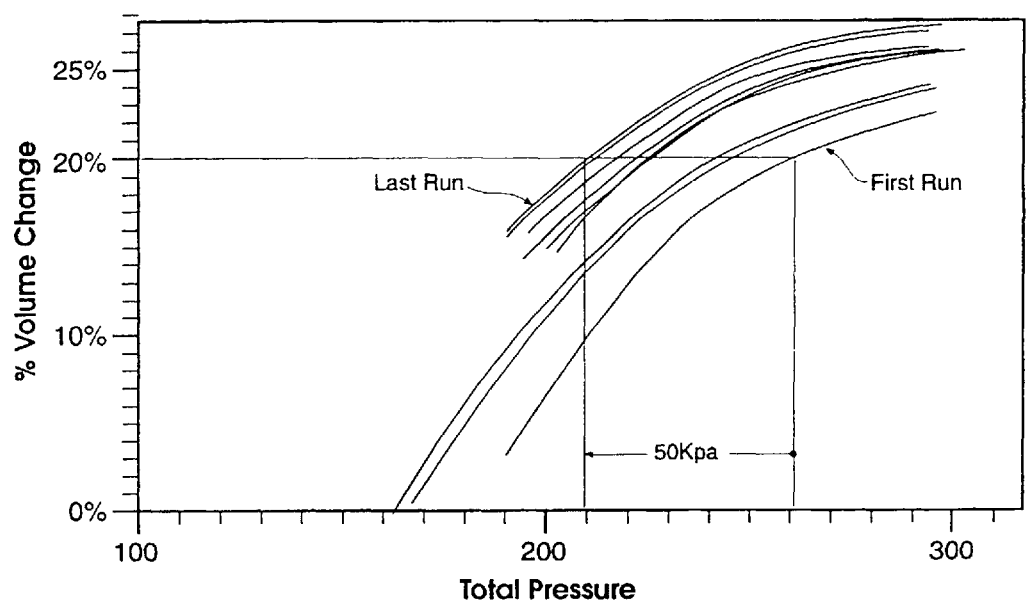

FIG. 17 is a graph as in FIG. 16 showing that there is some advantage in sensitivity if an offset pressure for a given volume of sensor (polyacrylamide) is approximately that of the matric potential to be measured in devices measuring 20 volume changes, FIG. 18 illustrates changes in response in some hydrogels (specifically polyacrylamides) over a two week period of repeated cycle times in which the first run was at the beginning and each reading showing a successive reading from one to two days apart to the last reading which was after fourteen days.

These results show a decrease in pressure sustaining capability of 50 kpa over the period of the test. This indicates that this material is less useful for longer term installations.

Figure 19:
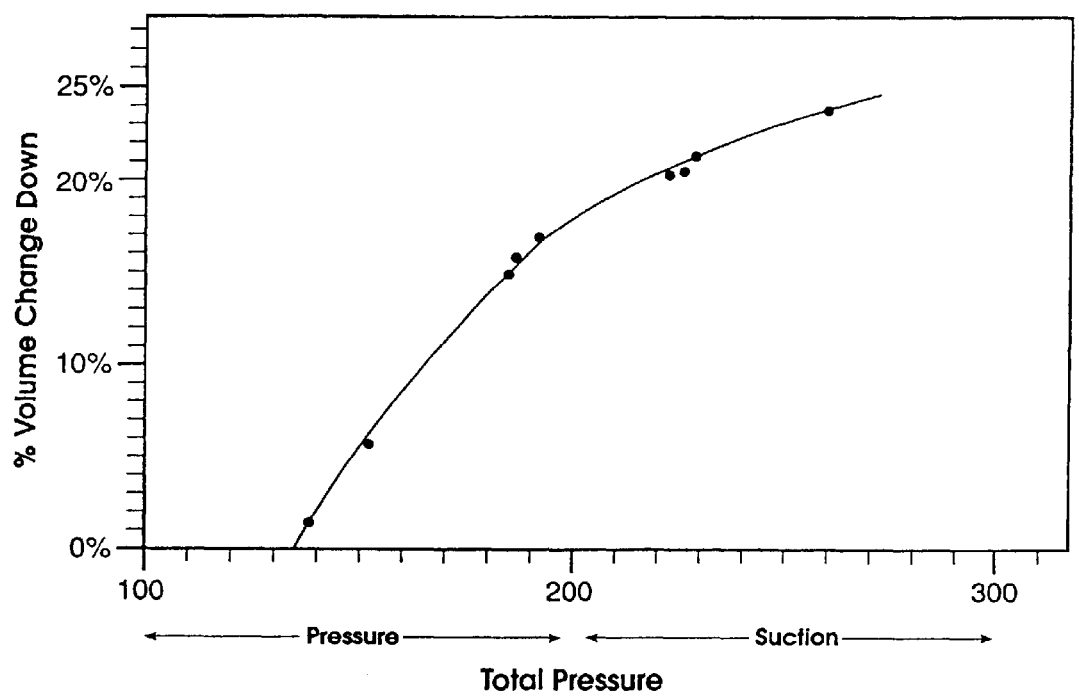

FIG. 19 illustrates how the responder material namely hydrogel will respond to both suction and pressure without distinction. This graph shows specific results using polyacrylate which as a material has shown more retention of its response effect over a period of time and would be the currently preferred material.

Referring to FIG. 1, this is a description of the prior art which is a conventional tensiometer where there is a closed tube 1 of a ceramic material which has within it water 2 and attached in a sealed relationship is a conduit 3 connected to a Bourden tube pressure measuring device 4.

The tube 1 is placed beneath the ground shown typically at 5 and the extent of suction of the soil will effect suction of the water 2 through the hydraulic communication provided by the ceramic tube 1 and this will be recorded as a suction pressure by the measuring device 4.

Typically, this type of device is limited by the vapor pressure of the water 2 which is about 80 kilopascals. Another difficulty is the possible entry of air through the ceramic. Both of these problems are overcome by the present invention.

A first embodiment of the current invention is shown schematically in FIG. 2. In this case there is provided a housing 10 which has within it a disc of hydrogel 11, a ceramic disc 12 on one side and separated by a pliable membrane 13, liquid mercury at 14.

A liquid mercury is connected through conduit 15 to a vertical tube 16, the upper end of which at 17 is open to atmosphere and the position of which is measured by calibrations shown at 18.

In this case the single disc of hydrogel is an ultra-high molecule weight a homopolymer of 2-hydroxyethyl methacrylate which is referred to briefly as "2-hema".

In this first embodiment then, the disc of 2-hema is subjected to pressure through the pliable membrane 13 of the head of mercury which is chosen to apply an appropriate pressure onto the 2-hema material so that water suction with which it will be in communication through a hydraulic connection through the ceramic material 12.

Because it has been discovered that there is a fixed relationship between pressure, volume and water content and that water content can be directly related to the matric potential of a medium with which it is in hydraulic communication, the hydrogel 11 in this case then will swell when communicating with a matric potential that is less than the physically applied pressure from the head of mercury. In this way then, there can be effected an output which is in relation to the head of mercury against the calibration which can be directly correlated with the matric potential of soil within which the housing 10 is located.

The calibrations in this embodiment are such that there will be shown a range of matric potential which will extend at least through the range of from 0 kilopascals to 100 kilopascals. The "2-hema" material in this case is a solid plastics material and it is held within the housing 10 by side walls 19 so that any expansion or contraction is constrained by reason of the close fitting sides and therefore expansion or contraction at right angles to the planar orientation of this material will be directly proportional to the increase in volume of the material.

FIG. 3 is a second embodiment which has substantially the same elements as in the first embodiment including a housing 20, a disc of hydrogel 21 which is the same material as used in the first embodiment namely 2-hema, and a pliable membrane 22.

A measure of the volume pressure relationship within the hydrogel 21 and the application of an applied compressive force is achieved in this case by use of a Bourden tube pressure gauge 23 connecting through a hydraulic link 24 to the chamber 25 within the housing 20.

There is a substantially incompressible liquid within the conduit 24 so that the traditional Bourden tube which has a flattened tube of spring material in a curved shape will then both enable the maintenance of a selected degree of pressure to be set through the fluid by calibrating the pressure gauge, and then allowing the pressure gauge to respond to changes in pressure which in turn will reflect changes in volume as compared to the applied pressure balanced against the detected matric potential of the medium within which the housing 20 is located so that the ceramic 26 can be in hydraulic communication with the medium.

FIG. 4 is a third embodiment in which there is a housing 30 within which there is an implanted piezo resistor 31 which is a known device which will provide a voltage output through its respective output leads 32 which voltage output is directly proportional to any applied pressure.

In this case, a hydrogel is again chosen which is 2-ultrahigh molecule weight homopolymer of 2-hydroxyethyl methacrylate of type G55 sold by Benz for the manufacture of contact lenses.

The material in the dry form is shredded into fine particles and is then saturated with water.

The material in this form shown at 33, is captured within a ceramic cap 34 which is then upside down to that position shown in FIG. 4. Screws including at 35 and 36 are used to squeeze excess of the material from between the mating surfaces of the housing 30 and the ceramic 34 and as this squeezing continues, apply a set pressure to the hydrogel 33.

Filling the space between the hydrogel 33 and the piezo resistor 31 is a silicon gel which is molded into the cavity within the housing 30 and is such that it will convey relatively directly, any pressure change effected by reason of even slight change in pressure in the hydrogel 33. This means that this is an almost entirely pressure responsive arrangement.

In a further embodiment not shown specifically in the drawings the alcosorb material has been replaced by 2=ultrahigh molecule weight homopolymer of 2-hydroxyethyl methacrylate of type G55 as described previously for the manufacture of contact lens which h&s shown some additional advantages. The material is precision machined to a predetermined size and placed in a cavity of the previous example in place of the alcosorb. The ratio of the volume of hydrogel to the volume of cavity determines the gel pressure in its saturated state.

The result of the arrangement shown then is that a capsule which can have very small dimensions indeed, can be located in any position where hydraulic communication can be effected with the ceramic material 34 and because there will be no necessity for a substantial change in volume to cause any change in pressure to be detected, such a device becomes very sensitive and very fast acting in response to changed conditions indeed.

The pressure sensor used in this embodiment has been obtained from SenSyn Inc of the USA. and is one of their SX series devices which have been modified in a way described to make it directly responsive to soil matric potential.

More particularly, the range of soil matric potential that can be detected and measured directly in this way is not limited to the range previously available only through a tensiometer and in trials conducted so far, a device of this type can be used to measure soil matric potential from close to 0 kilopascals to 10,000 kilopascals.

At the least then it provides a device to measure matric potential or soil suction as it is often referred to, in a range that is greater than 50 to 80 kilopascals.

Now referring to FIG. 5, this is a fourth embodiment which shows both a sensor and an actuator somewhat schematically where the actuator is arranged to control flow of water the extent of which then can be determined by a change in soil matric potential which is able to be detected by the sensor.

Describing this arrangement in detail, the sensor 40 includes a housing 41 which is made from a ceramic material which, as with the preceding ceramic materials described, are chosen and have a porosity such that they can provide good hydraulic communication with a soil within which they are placed.

In this case, the ceramic 41 is in the form of a cylinder having however a number of inner cavities which are each filled with fluidiz Alcosorb material as used in the last embodiment.

The fluidized Alcosorb material fills the plurality of cavities shown typically at 42 and is separated from chamber 43 by a membrane 44.

The membrane 44 in this case is cylindrical and is closed at an outer end by stopper 45 and at the other end by stopper 46 which also sealably connects conduit 47 to actuator 48.

The actuator 48 has a central plunger 49 adapted to move along a bore 50 within a housing 51.

The position of the plunger 49 is predominantly established by pressure exerted by spring 52 which acts to lift the plunger 49 and this is counted by any developed pressure within the conduit 47 delivered by way of the noncompressible liquid into chamber 53, This is kept sealed from the area providing the spring pressure by a pliable membrane 54.

The result of selected balance of pressure will be that the plunger 49 can cause the valve head 55 to be closed on valve seat 56 which will then interrupt flow of liquid through conduits 57 and 58.

The output of 58 is into a number of distribution heads typically and schematically shown at 59.

An effect of this arrangement is that a sensor can be located remotely from a directly operating actuator and that advantage can be achieved from the expanding volume as a result of increasing pressure within the hydrogel such that work can be effected by such a detected change.

A first setting of pressure on the hydrogel can be effected by choice of spring rate and tension in spring 49. (the loaded pressure of the spring in this embodiment is 2.2 kgs at a length of 25 mms and its unloaded length is 150 mms). (This means that there will be a relatively small change of pressure over modest displacements of the spring length so that this with the area of the diaphragm directly determines the operating range of the device with the spring movement). Accordingly the device can be set to operate over a selected range of pressures. In particular such an arrangement can work within the range of detected soil suction between 50 kilopascals to 300 kilopascals although it can also be used to operate in response to a wider range than this if needed.

An advantage of the fluidized hydrogel in this application is that it can be inserted into the labyrinth internal shape of the ceramic readily insofar that it acts like a fluid and further, there is a high degree of surface area as compared to hydrogel achieved in this arrangement which means that response times to any change in external environment can be quickly transferred and detected by the internal materials and further, can effect a sufficient change for substantial work to be output.

It will be noticed that the housing 48 is similar to an electrical coil of a type used conventionally as a solenoid controller for irrigation control valves so that it will be seen that the actuator in this case could directly replace such an electrically operated solenoid.

FIG. 6 is an enlargement of the actuator as shown in FIG. 5 and several additional features can be further therefore described including the conduit 60 providing atmospheric access to the chamber 50, the O-ring 61 which keeps water within the main supply conduit 57 sealably separate from the chamber 50, and there is shown an arrangement of springs 62 so as to transfer an effective pressure onto the valve head 56.

The feature of providing a closed liquid connection between the sensor and the actuator allows for a translation of an amount of volume change and pressure into any other combination of volume and pressure in a convenient way. It means also that results from the sensor can be transferred to a remote location without the need for a supply of electrical power.

FIG. 7 is a further embodiment which has an actuator very similar to the actuator described in the last embodiment but to which there is directly attached a sensor in accordance with the invention. The actuator then includes a housing 70 with a central rod 71 passing through a chamber 72 which is open to atmosphere as shown through conduit 73.

The rod 71 has at its end an arrangement 70 again providing for controlling of the position of valve head 75 with respect to valve seat 76.

This in turn then controls the flow of liquid from 77 through to 78.

The difference here however is that there is attached to the housing 70 a sensor housing 78 which holds a disk of porous ceramic 79 which holds, between itself and a membrane, a fluidized hydrogel 81 prepared in the manner described previously where Alcosorb was the material used.

As will now be seen, hydraulic communication can be achieved through the ceramic 79 into the hydrogel 81 and this will be sealed against transfer of liquids but nonetheless will transfer a change of pressure resulting in a volume change against spring pressure exerted by spring 82 of plate 83. This then allows for a setting of the spring with the quantity of material of hydrogel such that a preset pressure of perhaps 200 kilopascals can be applied which will then allow for the hydrogel to respond to changes in matric potential of about 100 kilopascals at which point the opening sequence will begin to control the passage of water effecting a watering program.

FIG. 8 is a cross-sectional view of an alternative sensor where the matric potential responding material is a solid hydrogel in this case 2-hema. In particular the sensor 90 includes an outer cylindrical housing 91 of a porous ceramic material adapted to provide a hydraulic communication between the environment in which it is inserted and an inner matric potential sensitive material shown at 92, The responding material in this case is a cylindrical slug of 2-hema with a hollow core.

In order for the solid slug to fit readily within the ceramic outer casing 91, this has a matching shape with however a plurality of circumferential slits shown typically at 93, each of these slits being filled with a wicking material which is chosen to be able to transfer in hydraulic manner matric potential from externally the sensor to the greater cross-sectional area of the responding material 92 in this way.

The cylindrical casing has an end cap 94 and a top cap 95 which holds therebetween a pliable membrane 96 which provides liquid isolation between the responding material 92 and an inner chamber area 97.

The inner chamber area 97 is mostly filled by a rod 98 which however has a conduit 99 which thereby provides communication for liquid held in a closed passageway for connection to an actuator.

As with the earlier embodiments, the matric potential responding material is chosen so that with appropriate application of hydraulic pressure, it can itself effect a volume pressure response which can be used to directly control an activator or of course any other device which it is useful to control in response to detected matric potential.

The range chosen for this particular embodiment also extends from 50 kilopascals to 300 kilopascals matric potential of the soil if the sensor is placed in the soil. FIG. 9 is a cross sectional view of a further sensor that can be used in conjunction with the fourth embodiment.

This then includes a non-porous housing 100 which has a cylindrically spaced cavity 101 in which there is a ceramic disk 102 which holds in place a slug of hydrogel of 2-ultra-high molecule weight homopolymer of 2-hydroxyethyl methacrylate which is fitted to nest tightly within the cylindrical shape of the cavity 101. There is a pliable membrane 103 which is captured between mating surfaces 104 of the housing 100.

The ceramic disk is rigid and holds the slug of 2-ultra-high molecule weight homopolymer of 2-hydroxyethyl methacrylate so that any change in volume will reflect in a proportionate change in the pressure against the membrane 103 and through this, against generally incompressible fluid 105 which is connected through conduit connections such as at 106 to an actuator where there will be applied a selected extent of pressure which is therefore applied to the 2-ultra-high molecule weight homopolymer of 2-hydroxyethyl methacrylate material. Any change in an extent of soil suction transmitted through the ceramic disk 102 is therefore transformed into a change in pressure in respect of the fluid 105.

Now referring to FIGS. 10 through to 13, these show a further embodiment which includes both an actuator 110 and a sensor 112.

The sensor 112 is arranged to control water flow passing through the sensor 112 out to a drain 113. The rate of flow is changed by varying resistance to flow provided by an opening of a valve (the actuator 110) to a mains supply of water so that with such a change to water flow this alters a balance of pressures in the actuator 110 and is arranged to change this from open to closed or from closed to open as the resistance to flow of water changes in the sensor 112.

In detail there is in the sensor 112 a non-glazed ceramic housing 114 which is therefore porous and will provide hydraulic communication (that is it will provide transfer of soil suction) to a material within the housing and especially the number of bores 115 passing deeply into the housing shape. These are 5 filled with an hydrogel specifically a cross linked polyacrylate (purchased from CIBA as Ciba Gelling agent 31). This is still a solid or gel but in this form is able to conform to a more complex shape such as that being shown in this example in the housing 114.

The hydrogel located within the respective bores 115 is held generally under a pressure which is applied by reason of spring 116 which is supported so as to press against a transversely extending pin which is arranged to pass through piston 119 and so that the spring and the membrane will act directly against the hydrogel in the bores 115.

This pressure being applied specifically by the spring 116 will, as appropriate, be opposed by a decreasing extent of soil suction which will hydraulically communicate through the porous interstices of the ceramic housing 114.

The pin 117 is embedded within piston 119 which has an aperture 120 passing through it, through which the arm 121 passes through thereby engaging against the bottom of the pin 117 and thereby providing a force depending upon the spring rate and the extent to which the shaft 138 and the spring 116 is tightened or loosened whereby to alter the spring force.

The sensor 112 as a whole is supported by a general housing 122 which has a conduit 123 connecting to the actuator 110 and a drain 113.

There is a bellows 124 which is arranged to have its inside volume in communication with liquid passing through conduit 123 and in particular tube 125 which is arranged so that, with an increase in pressure within the conduit 123, there will be an effective increase in pressure within the bellows 124. As this is made up of two parts which are resiliently retained in a first retracted position, this will be urged to expand with increased relative pressure.

Such an increased relative pressure will occur when the piston 119 is urged into closer relative positioning with respect to seat 126.

The effect then is that with a modest increase in resistance to water flow through conduit 123, there will be caused firstly an increase in expansion of the bellows 124 which will further raise the outlet provided by the seat 126 and this in effect causes a snap action closure.

Such a closure then effects a total closure of liquid passing through conduit 123 which then causes the pressure within chamber 130 in the actuator 110 to increase in that there is no longer a draining of liquid from this chamber through the conduit 123. This in turn then will cause a build-up of such pressure to effect a closing of the main valve 131 thereby closing a main supply.

Accordingly, there is provided a slaving arrangement operated by the sensor 112 which is efficiently caused to have a snap action depending upon the status of pressure relatively provided by hydrogel within the ceramic housing 114.

The actuator 110 is a relatively standard mains control valve which includes a mains water passageway 132 which passes through seat 133 to outlet 134.

Conduit 135 is a feature of a standard valve which is closed off for this operation and replaced by vent 113. Accordingly liquid feeding through gap 137 will either build-up or reduce pressure within the chamber 130 as compared to the rate of discharge through the outlet 133.

This comparative ratio is, of course, varied by providing additional or reduced lead off externally and hence the sensor 112 can be caused to be a very effective controller.

A few points that are of note include the fact that the piston 119 does not respond and need not respond through a complete range of movements in direct response to soil matric potential but only to that extent of movement which is in the range of the spring movement available and hence can be caused to operate at a selected extent of soil matric potential.

FIG. 10 indicates the relative positioning of the moveable parts when the soil matric potential is high and therefore the piston 119 is kept raised and accordingly it will be seen that the main valve 131 is open with therefore passage available of mains water through the mains conduit 132.

FIG. 12 illustrates the opposite position in which there is a higher degree of moisture in the soil and there is, therefore, a greater degree of saturation which is transmitted hydraulically through the porous ceramic housing to the hydrogel which in turn then is under more externally applied pressure through the spring 116.

This, however, effects the closure of the conduit 123 and hence the balance of pressures operating within the chamber 130 is such that the main valve 131 is closed thereby blocking mains water supply.

In FIG. 13, this illustrates, from a plan view, the spring 116 and its relationship with the piston 119 and, as will be seen, the spring 116 is wound around a rod 138 which is held under a friction grip by grip 139 but such that the rod 138 can be rotated against resistance about its axis so that it can wind tighter or looser the spring 116 about the rod 138.

Such a setting can be controlled from an external access to aperture 140 by an allen key.

With the arrangement described, a member 141 is simply a plug that is able to be sealably screwed into the top of the actuator valve 110 which is connected with a supply of liquid through to the sensor 112.

This plug 141 simply replaces a standard electrical solenoid of a type that is relatively standard as used in many irrigation installations.

Accordingly there is provided a controller for such valves which can accurately respond to a selected extent of soil matric potential which does not require an electrical supply and which can be connected at any location where an appropriate conduit can be connected for transfer of liquid flow.

One of the advantages of using a ceramic housing where there are a number of separate bores is that this allows for substantial distribution of the hydrogel material where the housing itself will distribute through its porous hydraulic communication, the effect of the soil matric potential to a high surface area available of hydrogel.

Further, the fact that the housing itself is a single element which can be cast, means that such a unit can be economically manufactured for this application.

One of the advantages of having the snap action provided by the expanding or reducing bellows is that this can mean that when a mains water supply is being controlled by the sensor as described, then if the water supply is being distributed by, for instance, a sprinkler the spread of water will be maintained relatively constant until the sensor snaps into a closed position at which stage the water flow will be stopped and, of course, the sprinkler will not be operated at a pressure which would be wasteful of water or uneconomic.

This is not always necessary in the case, for instance, of a dripper alignment where lower pressures of water can be acceptable but, even in such instances, it is considered better generally to have either a full flow mains pressure or no flow at all. This effective in reducing fouling problems in water supplies containing small particles.

FIG. 14 illustrates, in a schematic way, a test rig that has been set up to test the characteristics of appropriate materials for the application of the water soluble material.

Some materials are discovered as being better for the application than others.

Currently all hydrogels that have been tested have been able to illustrate the effect which is that they will exhibit a change in internal pressure which is in response to externally applied mechanical pressure and an extent of soil suction to which the material is connected.

This effect then results in a relative internal pressure result which can either be read directly or can be determined by measuring an extent of volume change against internal resilient or other resistance.

This then distinguishes this concept from any case where there is merely a slug of material which is known to swell or to contract with exposure to water.

Here in FIG. 14, there is now described a test rig by which materials can be tested as to their appropriateness for the application.

Accordingly, there is a supply of air at pressure through valve 150 and pressure regulator 151 with, however, an accurate pressure measuring device at 153 and an accurate displacement measuring device at 154.

The test rig itself includes a cylindrical housing at 155 with an upper cap at 156 and a lower cap at 157.

The ceramic housing at 158 being shown in this instance, is the same as shown in the last described embodiment, with a number of deep bores drilled into a porous ceramic material and this is filled with the hydrogel or other material on test shown generally at 159.

Soil matric potential is simulated by effecting a suction through conduit 160 which, however, is maintained through applying the lower pressure into space 161 so that the reduced pressure is applied through reduction of pressure in water 162 which then is applied as a saturated liquid surround at 163 which applies the selected extent of suction.

The accurate extent of suction is determined by accurate mercury manometer 164.

Now, as we apply a selected extent of pressure such as, for instance, 300 kilopascals through the conduit 165 in the first instance and then apply a change in effective suction, the resulting change in pressure as well as the extent of change in volume can then be accurately determined.

As can now be seen, the degree of tension applied can be read from mercury manometer 164.

To ensure that a match of calibration is achieved for a degree of pressure applied, the pressure is determined by the mercury manometers 153 and 164.

The change in volume of any hydrogel or other material on test is read by a change in the level of the sight glass of water within 154 as water is moved into a chamber behind diaphragm 156 and into space originally occupied by the material on test. The ceramic disk 156a provides a support for the diaphragm 156 in a back pressure situation.

Using this test rig, it has been discovered that the material on test especially hydrogels, are responding to the differential pressure applied either side of the ceramic interface and that there has been no distinction between the levels of positive and negative pressure applied in regard to the degree of volume change of the material on test.

From this, I have deduced that the method of loading the material on test has been especially relevant to accurate measurement. It has been found, for instance, that an applied pressure to the material on test is a useful way of setting a measuring range of a sensor as the pressure applied to saturated material on test at 0 kpa tension determines the degree of tension that would need to be applied to the material on test in a chamber of fixed volume before the internal pressure of the material on test reached 0 KpaG.

When a constant pressure is applied to the material on test, while it is subjected to tension forces, the volume occupied by the material will reduce by a same amount for say 100 Kpa tension as for an increase of 100 Kpa in the pressure applied. I therefore say that by using such a technique, a person who wishes to establish an appropriateness of a particular material for the purpose can now determine this through this accurate but relatively simple test rig device.

FIG. 15 is a graphical representation of a sensor material in volume in cubic centimeters against the load applied in Kilopascals, the result of measurements of the matric potential material namely the hydrogels which have been used and it illustrates the way in which there is a relationship between the kilopascals load and the volume of the sensor material.

I now refer to the graphs in FIGS. 16, 17.

In FIG. 16, this illustrates the tests that have been conducted, showing percentage volume change as compared to total pressure for a first selected material on test namely polyacrylamide.

The method of test has been as follows;

Water is added to a selected quantity of polyacrylamide particles so that it has more water than would be required to support 100 kpa. The material is placed in a container which has an outlet for the material in the water ingested state at its bottom, and an inlet for air at the top of the container.

The outlet is connected to a sensor cavity of a porous housing which is at first filled with water to eliminate air. When pressure is applied to the top of the hydrogel at 100 kpa, the material will enter the cavity displacing the water.

Water will then be expelled from the hydrogel material through the permeable walls of the cavity until the material remaining will support 100 kpa without further loss of water. A combination of suction and pressure are applied to the hydrogel material, suction from outside the cavity and pressure by way of an isolating diaphragm to the inside of the cavity. With combinations of pressure and suction in excess of 100 kpa additional water will be expelled from the material with a resultant change in volume indicated by a sight glass connected on the outside of the diaphragm.

The results using this method shows then that where there is a 10 percent pressure increase the sensor material volume changes will decrease with additional loading so that if the additional load increases by say 50 kilopascals, then an additional 50 kilopascals of change in sensor pressure, which is the equivalent of soil matric potential, will be required.

In FIG. 17, there again is shown a relationship discovered for a further material namely polyacrylamide showing the volume changes for applied total pressures.

As will now be seen, the invention can be variously applied and various materials are useful.

Reference has been made to three hydrogels which can be usefully incorporated in to the concept of this invention.

Other examples of hydrogels which are considered to be useful in the applications include an ultra-high molecular weight copolymer of 2-hydroxyethyl methacrylate and N-vinyl pyrolidone and in another case, a copolymer of 2,3-dihydroxypropyl methacrylate and 2-hydroxyethyl methacrylate.

Preferred hydrogels have characteristics that allow them to be used over a significant period of time in the application and provide a sufficient response within the most useful range of from 50 kilopascals to 300 kilopascals.

Some hydrogels might not be suitable in an actual application where they are going to be exposed to bacterial attack where they might need to last for some longer period of time in a damp environment.

The output from any of the described embodiments can have electrical contacts for effecting electrical switching.

I claim:

1. A matric potential responder including comprising a housing, which is sealed, apart from one part of the housing being porous to provide for the effect of matric potential within soil to transfer therethrough, a liquid absorbing swellable non-liquid material selected to exhibit an increase or decrease in expansive pressure in response to any matric potential of the hydraulically connected materials, said swellable non-liquid material held with the housing under a predetermined range of compressive pressures and output means adapted to effect an electrical output in response to changes in magnitude of pressure exerted by said material when compressed.

2. A matric potential responder as in claim 1 wherein the liquid absorbing swellable non-liquid material is a hydrogel.

3. A matric potential responder as in claim 2 wherein the hydrogel is taken from the group consisting of a polyacrylate and an ultra-high molecular weight homopolymer of 2-hydroxyethyl methacrylate.

4. A matric potential responder as in claim 3 wherein the hydrogel is selected from the group consisting of (a) an ultra-high molecular weight copolymer of 2-hydroxyethyl methacrylate and N-vinyl pyrolidone and (b) a copolymer of 2,3-dihydroxypropyl methacrylate and 2-hydroxyethyl methacrylate.

5. A matric potential responder as in claim 2 wherein the hydrogel is in one piece.

6. A matric potential responder as in claim 2 wherein the hydrogel is a plurality of pieces that can be filled into an internal chamber to collectively take on a shape complementary to a shape of the internal chamber.

7. A matric potential responder as in claim 1 wherein the output means includes a transducer in the form of a piezo resistor.

8. A matric potential responder as in claim 7 wherein the piezo resistor is provided with a support that bows under pressure exerted by the hydrogel, the piezo resistor giving an output corresponding to the degree of bowing.

9. A matric potential responder as in claim 1 wherein the porous part of the housing is a baked and unglazed ceramic material.

10. A matric potential responder as in claim 1 wherein the material selected and the compressive pressure applied are such that the responder will provide an output to detected matric potential at least within a range of from 50 kilopascals to 300 kilopascals.

11. A matric potential responder as in claim 1 wherein the output means includes a pair of alternately openable and closable electrical contacts.

12. A matric potential responder as in claim 1 wherein the housing is rigid and the swellable non-liquid material is constrained, at least after the initial expansion, to a substantially fixed volume over an entire range of matric potentials over which the responder operates.

13. A matric potential responder as in claim 1 wherein the housing is rigid and the swellable non-liquid material is constrained, at least after the initial expansion, to a substantially fixed volume over an entire range of matric potentials over which the responder operates.

14. A matric potential responder comprising:

a substantially sealed housing having a porous part for enabling a transfer into the housing of a matric potential existing within ambient soil;

a liquid absorbing swellable non-liquid material selected to exhibit an increase or decrease in expansive pressure in response to a change in the matric of the ambient soil, said swellable non-liquid material being held with the housing under a predetermined range of compressive pressures; and an electrical circuit disposed in said housing in effective contact with said swellable nonliquid material for generating an electrical output in response to changes in magnitude of pressure exerted by said swellable non-liquid material.

15. A matric potential responder as in claim 14 wherein the liquid absorbing swellable non-liquid material is a hydrogel.

16. A matric potential responder as in claim 15 wherein the hydrogel is taken from the group consisting of a polyacrylate and an ultra-high molecule molecular weight homopolymer of 2-hydroxyethyl methacrylate.

17. A matric potential responder as in claim 15 wherein the hydrogel is selected from the group consisting of (a) an ultra-high molecular weight copolymer of 2-hydroxyethyl methacrylate and N-vinyl pyrolidone and (b) a copolymer of 2,3-dihydroxypropyl methacrylate and 2-hydroxyethyl methacrylate.

18. A matric potential responder as in claim 15 wherein the hydrogel is in one piece.

19. A matric potential responder as in claim 15 wherein the hydrogel is a plurality of pieces introduceable into an internal chamber to collectively take on a shape of the internal chamber.

20. A matric potential responder as in claim 14 wherein the electrical circuit includes a transducer in the form of a piezo resistor.

21. A matric potential responder as in claim 20 wherein the piezo resistor is provided with a support that bows under pressure exerted by the hydrogel, the piezo resistor giving an output corresponding to the degree of bowing.

22. A matric potential responder as in claim 14 wherein the porous part of the housing is a baked and unglazed ceramic material.

23. A matric potential responder as in claim 14 wherein the swellable non-liquid material and the compressive pressure applied are such that the responder will provide an output to detected matric potential at least within a range of from 50 kilopascals to 300 kilopascals.

24. A matric potential responder as in claim 14 wherein the electrical circuit includes a pair of alternately openable and closable electrical contacts.

* * * * *